US009636364B2

(12) United States Patent
Brown et al.

(10) Patent No.: US 9,636,364 B2
(45) Date of Patent: May 2, 2017

(54) METHODS FOR TREATING OCULAR CONTUSION AND BLUNT INJURY AND TRAUMATIC INJURY TO THE OPTIC NERVE

(71) Applicant: Stemnion, Inc., Pittsburgh, PA (US)

(72) Inventors: Larry R Brown, Newton, MA (US); George L Sing, New York, NY (US); Howard C Wessel, Kensington, PA (US)

(73) Assignee: STEMNION, INC., Pittsburgh, PA (US)

(*) Notice: Subject to any disclaimer, the term of this patent is extended or adjusted under 35 U.S.C. 154(b) by 0 days.

(21) Appl. No.: 14/556,300

(22) Filed: Dec. 1, 2014

(65) Prior Publication Data
US 2015/0150915 A1 Jun. 4, 2015

Related U.S. Application Data

(60) Provisional application No. 61/911,653, filed on Dec. 4, 2013, provisional application No. 61/911,660, filed on Dec. 4, 2013.

(51) Int. Cl.
A61K 35/50 (2015.01)
A61K 38/19 (2006.01)
A61K 9/00 (2006.01)
A61K 9/19 (2006.01)

(52) U.S. Cl.
CPC ............ *A61K 35/50* (2013.01); *A61K 9/0043* (2013.01); *A61K 9/0046* (2013.01); *A61K 9/19* (2013.01); *A61K 38/19* (2013.01)

(58) Field of Classification Search
None
See application file for complete search history.

(56) References Cited

U.S. PATENT DOCUMENTS

| 2004/0057938 | A1* | 3/2004 | Ghinelli | A61K 35/48 424/93.7 |
|---|---|---|---|---|
| 2006/0222634 | A1 | 10/2006 | Clarke et al. | |
| 2007/0231297 | A1 | 10/2007 | Smith et al. | |
| 2008/0286267 | A1* | 11/2008 | Sing | A61K 35/48 424/130.1 |
| 2009/0054339 | A1 | 2/2009 | Marshall et al. | |
| 2009/0075381 | A1 | 3/2009 | Marshall et al. | |
| 2010/0075905 | A1 | 3/2010 | Marshall et al. | |
| 2010/0080779 | A1 | 4/2010 | Smith et al. | |
| 2010/0144604 | A1 | 6/2010 | Marshall et al. | |
| 2011/0158958 | A1* | 6/2011 | Sing | A61K 35/50 424/93.7 |
| 2012/0101036 | A1 | 4/2012 | Smith et al. | |
| 2012/0225048 | A1 | 9/2012 | Marshall et al. | |
| 2012/0225815 | A1 | 9/2012 | Smith et al. | |
| 2012/0230941 | A1 | 9/2012 | Sing et al. | |
| 2012/0238495 | A1 | 9/2012 | Smith et al. | |
| 2012/0251526 | A1 | 10/2012 | Smith et al. | |
| 2012/0270319 | A1 | 10/2012 | Clarke et al. | |
| 2012/0322731 | A1 | 12/2012 | Marshall et al. | |
| 2013/0040880 | A1 | 2/2013 | Marshall et al. | |
| 2013/0071363 | A1 | 3/2013 | Smith et al. | |
| 2013/0071364 | A1 | 3/2013 | Smith et al. | |
| 2013/0115197 | A1 | 5/2013 | Emig et al. | |
| 2013/0302307 | A1 | 11/2013 | Trumpower et al. | |
| 2014/0017193 | A1 | 1/2014 | Sing et al. | |
| 2014/0079688 | A1 | 3/2014 | Sing et al. | |
| 2014/0242043 | A1 | 8/2014 | Steed et al. | |
| 2014/0255355 | A1 | 9/2014 | Sing et al. | |
| 2015/0025007 | A1 | 1/2015 | Emig et al. | |
| 2015/0050251 | A1 | 2/2015 | Trumpower et al. | |
| 2015/0202235 | A1 | 7/2015 | Emig et al. | |
| 2016/0220615 | A1 | 8/2016 | Sing | |

FOREIGN PATENT DOCUMENTS

| WO | WO 2006/105152 | 10/2006 |
|---|---|---|
| WO | WO 2009/008928 | 1/2009 |
| WO | WO 2009/025730 | 2/2009 |

OTHER PUBLICATIONS

Stedman's Online Medical Dictionary. Bruise.Contusion. Datasheet [online]. Stedman's Online. [retrieved on Mar. 5, 2016]. Copyright 2009. Lippincott Williams & Wilkins. Retrieved from the Internet: <URL:http://www.stedmansonline.com/popup.aspx&aid=517024> and >=5178127> pp. 1, 2.*
Ross, T.M. 2004. Intranasal administration of interferon beta bypasses the blood-brain barrier to target the central nervous system and cervical lymph nodes: a non-invasive treatment strategy for multiple sclerosis. Journal of Neuroimmunology 151: 66-77. specif. pp. 66, 67, 70, 76, 76.*
Kublik, H. et al. 1998. Nasal delivery systems and their effect on deposition and adsorption. Advanced Drug Delivery Reviews 29: 157-177. specif. pp. 157, 160, 161, 164, 166.*
Chen, Z. et al. Nov. 2009. Human amnion-derived multipotent progenitor cell treatment alleviates traumatic brain injury-induced axonal degeneration. Journal of Neurotrauma 26: 1987-1997. specif. pp. 1987, 1988, 1989.*
Compston, A. 2004. Mechanisms of axon-glial injury of the optic nerve. Eye 18: 1182-1187. specif. pp. 1182, 1183.*

(Continued)

*Primary Examiner* — Renee Claytor
*Assistant Examiner* — Sharon M Papciak
(74) *Attorney, Agent, or Firm* — Linda O. Palladino; Gail M. Kempler

(57) ABSTRACT

The invention is directed to methods for treating ocular contusion and blunt injury to the eye and for treating traumatic injury of the optic nerve. The invention is further directed to treating ocular contusion and blunt injury to the eye and for treating traumatic injury of the optic nerve by administering to a subject suffering from such conditions Amnion-derived Cellular Cytokine Solution (ACCS), including immediate-release, targeted-release, and sustained-release (SR) ACCS compositions (referred to herein as "SR-ACCS" compositions) and/or Amnion-derived Multipotent Progenitor (AMP) cell compositions. Such administration includes intranasal administration of ACCS and/or AMP cells.

14 Claims, No Drawings

(56) References Cited

OTHER PUBLICATIONS

Miki, T. et al. 2005. Stem cell characterisitics of amniotic epithelial cells. Stem Cells 23: 1549-1559. specif. p. 1549.*

Meyer, C.H. et al. 2003. Acute commotio retinae determined by cross-sectional optical coherence tomography. European Journal of Ophthalmology 13(9/10): 816-818. specif. p. 816.*

Stedman's Online Medical Dictionary. Concussion. Datasheet [online]. Stedman's Online. [retrieved on Oct. 26, 2016]. Copyright 2009. Lippincott, Williams & Wilkins. Retrieved from the Internet: <URL:http://www.stedmansonline.com/popup.aspx?aid=5177564> p. 1.*

* cited by examiner

METHODS FOR TREATING OCULAR CONTUSION AND BLUNT INJURY AND TRAUMATIC INJURY TO THE OPTIC NERVE

FIELD OF THE INVENTION

The field of the invention is directed to methods for treating ocular contusion and blunt injury to the eye and for treating traumatic injury of the optic nerve. The field of the invention is further directed to treating ocular contusion and blunt injury to the eye and for treating traumatic injury of the optic nerve by administering to a subject suffering from such conditions Amnion-derived Cellular Cytokine Solution (ACCS), including novel immediate-release, targeted-release, and sustained-release (SR) ACCS compositions (referred to herein as "SR-ACCS" compositions) and/or and Amnion-derived Multipotent Progenitor (AMP) cell compositions. Such administration includes intranasal administration of ACCS and/or AMP cells.

BACKGROUND OF THE INVENTION

Blast and blunt injuries to the eye can cause a series of mechanical disruptions to the ocular contents including: commotio retinae, traumatic cataract, disruption of the zonular attachments to the lens, angle recession, iris dialysis, and rupture of the pupillary sphincter. Treatment of these injuries has been limited to mechanical repair (when possible) of the iris, replacement of the crystalline lens with plastic lens implants, and repair of retinal detachments. There has been no treatment to repair the cellular architecture of the retina or the anterior chamber. Amnion-derived Cellular Cytokine Solution (ACCS), a novel multi-factorial solution of cytokines, growth factors, lipids, micro-RNAs, amino acids and vitamins, made from cultured Amnion-derived Multipotent Progenitor (AMP) cells, has been shown to foster limited regeneration of brain tissue architecture after injury (Z. Chen, F. C. Tortella, J. R. Dave, V. S. Marshall, D. L. Clarke, G. Sing, F. Du, X.-C. M. Lu, Human amnion-derived multipotent progenitor cell treatment alleviates traumatic brain injury-induced axonal degeneration, J. Neurotrauma 26, 1987-97 (2009); Ying Deng-Bryant, PhD, Zhiyong Chen, PhD, Christopher van der Merwe, BS, Zhilin Liao, MS, Jitendra R. Dave, PhD, Randall Rupp, PhD, Deborah A. Shear, PhD, and Frank C. Tortella, PhD, Long-term administration of amnion-derived cellular cytokine suspension promotes functional recovery in a model of penetrating ballistic-like brain injury, J. Trauma Acute Care Surg 73(2) Supplement 1, 156-164, 2012), all of which are incorporated herein by reference in their entirety. It also contains many of the proteins found in tears including mucins and Tissue Inhibitors of Metalloproteinases-1 and 2 (TIMP-1 and TIMP-2). ACCS is anti-inflammatory and is favorable to cellular regeneration which may unlock the keys to regeneration of traumatized eye tissues previously thought to be irreparable. In addition, ACCS is anti-inflammatory and anti-apoptotic for certain neuronal cells (Z. Chen, F. C. Tortella, J. R. Dave, V. S. Marshall, D. L. Clarke, G. Sing, F. Du, X.-C. M. Lu, Human amnion-derived multipotent progenitor cell treatment alleviates traumatic brain injury-induced axonal degeneration, J. Neurotrauma 26, 1987-97, 2009). Apoptosis has been implicated as a primary cause of photoreceptor cell death as a result of retinal detachment (Murakami, Y., Notomi, S., Hisatomi, T., Nakazawa, T., Ishibashi, T., Miller J., and Vavvas, D. Photoreceptor cell death and rescue in retinal detachment and degenerations., Progress in Retinal and Eye Res., 37, 114-140, 2013), incorporated herein by reference in its entirety.

Traumatic optic neuropathy and optic nerve avulsion are among the six leading types of ocular injury that required specialized ophthalmic care during Operation Iraqi Freedom (Cho and Savitsky, "Ocular Trauma Chapter 7", in Combat Casualty Care: Lessons learned from Oef and Oif, by Brian Eastbridge and Eric Savitsky, pp. 299-342, Ft. Detrick, Md.: Borden Institute (US) Government Printing Office, 2012), incorporated herein by reference in its entirety. Sixty percent of traumatic head injuries result in neuro-ophthalmic abnormalities (Van Stavern, et al., "Neuro-Ophthalmic Manifestations of Head Trauma", J Neuro-Ophthamol 21(2):112-117, 2001) (incorporated herein by reference in its entirety) half of which involve the optic nerves or visual pathways. Traumatic injury to neurons results in axonal damage and irreversible neuronal loss resulting in permanent deficits. While a number of potential neuroprotective therapies have been identified in animals, these single agents have universally failed to translate to therapies in human clinical trials (Turner, et al., "The science of cerebral ischemia and the quest for neuroprotection: navigating past failure to future success", J Neurosurg 118(5):1072-1085, 2013, incorporated herein by reference in its entirety). Combination therapies that affect several cellular targets are likely needed to prevent neuronal damage.

Delivery of a drug to the optic nerve is clearly difficult. Proteins can be delivered non-invasively via the intranasal route to the optic nerve and the central nervous system (CNS) (Ross, et al., "Intranasal administration delivers peptoids to the rat central nervous system", Neuroscience Letters 439:30-33, 2008; Zuo, et al., "SIRT1 promotes RGC survival and delays loss of function following optic nerve crush", Invest Ophthalmol Vis Sci 54(7):5097-5102, 2013), incorporated herein by reference in their entirety. Intranasal insulin has been successfully delivered to the CNS in clinical trials for the treatment of Alzheimer's disease (Craft, et al., "Intranasal insulin therapy for Alzheimer Disease and amnestic mild cognitive impairment", Arch Neurol 69(1): 29-38, 2012), incorporated herein by reference in its entirety.

BRIEF SUMMARY OF THE INVENTION

Applicant's invention is directed to the use of ACCS, a novel biologic, or AMP cells, a novel cell population, for treating ocular contusion and blunt injury to the eye. Applicant's invention is also directed to the use of ACCS or AMP cells, both delivered via the intranasal route, to ameliorate ophthalmic neural degeneration in a traumatic injury model of the optic nerve. Details on ACCS can be found in U.S. Pat. No. 8,088,732 and details on AMP cells can be found in U.S. Pat. No. 8,278,095 (both of which are incorporated herein by reference in their entirety). Applicant has previously demonstrated that ACCS promotes neuro-protective functional recovery in a rat penetrating ballistic-like traumatic brain injury model (see U.S. Pat. No. 8,197,804, incorporated herein by reference in its entirety). Applicant has also demonstrated that ACCS is anti-inflammatory in several settings and can alleviate neurite degeneration in an in vitro apoptotic cell death model (Chen, et al., Differential effects of human Amnion-derived Multipotent Progenitor Cells and Amnion-derived Cellular Cytokine Solution (ACCS) in traumatic brain injury, submitted, 2013, incorporated herein by reference in its entirety). The delivery of ACCS to the optic nerve could potentially protect or ameliorate optic nerve damage.

In addition, Applicant has discovered that ACCS and AMP cells exhibit many wound healing properties. Thus ACCS and/or AMP cells delivered topically to the eye may help treat ocular contusion and blunt injury of the eye. In addition, ACCS and/or AMP cells, delivered into the nasal cavity, for example as a liquid nasal spray, would be expected to be an effective means for treating traumatic injury of the optic nerve or ameliorating optic nerve degeneration by placing the compositions onto the nasal mucosa which is adjacent to the foramina of the cribriform plate located at the superior aspect of the nasal cavity. Such administration would allow the ACCS and/or AMP cell compositions to permeate through the foramina into the cranial cavity at the location of the optic nerve.

The instant invention provides novel immediate-release, targeted-release, and sustained-release ACCS and/or AMP cells for use in the methods. Because the cellular factors are present in the ACCS or secreted by the AMP cells at levels comparable to physiological levels found in the body, they are optimal for use in therapeutic applications which require intervention to support, initiate, replace, accelerate or otherwise influence biochemical and biological processes involved in the treatment and/or healing of injury. In the case of the slow-release compositions, the cellular factors are released slowly over time to provide a continual, consistent physiologic level of such factors to optimize healing and/or recovery. The AMP cells also release their cellular factors over time.

Accordingly, a first aspect of the invention is a method for treating ocular contusion and blunt injury to the eye in a patient in need thereof comprising administering to the patient a therapeutically effective amount of a composition selected from the group consisting of Amnion-derived Cellular Cytokine Solution (ACCS) and Amnion-derived Multipotent Progenitor (AMP) cells.

A second aspect of the invention is a method for treating traumatic injury of the optic nerve in a patient in need thereof comprising administering to the patient a therapeutically effective amount of a composition selected from the group consisting of Amnion-derived Cellular Cytokine Solution (ACCS) and Amnion-derived Multipotent Progenitor (AMP) cells.

A third aspect of the invention is a method for ameliorating optic nerve degeneration in a patient in need thereof comprising administering to the patient a therapeutically effective amount of a composition selected from the group consisting of Amnion-derived Cellular Cytokine Solution (ACCS) and Amnion-derived Multipotent Progenitor (AMP) cells.

A specific embodiment of aspects 1-3 of the invention is one wherein the ACCS or the AMP cells are formulated for intranasal administration, topical administration or administration by intraocular injection.

Another specific embodiment of aspects 1-3 of the invention is one wherein the intranasal administration is aerosol or spray administration.

Another specific embodiment of aspects 1-3 of the invention is one wherein the ACCS is formulated as a lyophilized dry powder nasal formulation.

The above-described aspects and embodiments are not intended to be limiting in any way, merely exemplary. Skilled persons will recognize that other aspects and embodiments, though not explicitly stated, are non-the-less contemplated by and encompassed by the invention.

DEFINITIONS

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristics of secreting a unique combination of physiologically relevant cytokines in a physiologically relevant temporal manner into the extracellular space or into surrounding culture media and which have not been cultured in the presence of any animal-derived products, making them and cell products derived from them suitable for human clinical use. In a preferred embodiment, the ECS cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2. The ECS cells may optionally express Thymosin β4.

As used herein, the term "Amnion-derived Multipotent Progenitor ell" or "AMP cell" means a specific population of ECS cells that are epithelial cells derived from the amnion. In addition to the characteristics described above for ECS cells, AMP cells have the following characteristics. They have not been cultured in the presence of any non-human animal-derived products, making them and cell products derived from them suitable for human clinical use because they are not xeno-contaminated. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion epithelial cells, from which AMP cells are selected, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and novel populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to, hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from ECS cells, including AMP cells.

As used herein, the term "Amnion-derived Cellular Cytokine Solution" or "ACCS" means conditioned medium that has been derived from AMP cells.

As used herein, the term "suspension" means a liquid containing dispersed components, i.e. cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In certain instances it may be desirable to retain the cell membrane fraction.

The term "physiologic" or "physiological level" as used herein means the level that a substance in a living system is found and that is relevant to the proper functioning of a biochemical and/or biological process.

As used herein, the term "substrate" means a defined coating on a surface that cells attach to, grow on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "therapeutically effective amount" means that amount of a therapeutic agent necessary to achieve a desired physiological effect (i.e., treating ocular contusion and blunt injury to the eye or traumatic injury to the optic nerve).

As used herein, the term "pharmaceutically acceptable" means that the components, in addition to the therapeutic agent, comprising the formulation, are suitable for administration to the patient being treated in accordance with the present invention.

As used herein, the term "therapeutic component" means a component of the composition which exerts a therapeutic benefit when the composition is administered to a subject.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time-release capsules and the like.

The terms "parenteral administration" and "administered parenterally" are art-recognized and refer to modes of administration other than enteral and topical administration, usually but not necessarily by injection, and includes, without limitation, intravenous, intramuscular, intraarterial, intrathecal, intracapsular, intraorbital, intraocular, intracardiac, intradermal, intraperitoneal, transtracheal, subcutaneous, subcuticular, intra-articulare, subcapsular, subarachnoid, intraspinal, epidural, intracerebral, intranasal, and intrasternal injection or infusion.

As used herein, the term "aerosol" means a cloud of solid or liquid particles in a gas.

The terms "particles", "aerosolized particles", and "aerosolized particles of formulation" are used interchangeably herein and shall mean particles of formulation comprised of any pharmaceutically active ingredient, preferably in combination with a carrier, (e.g., a pharmaceutically active respiratory drug and carrier). The particles have a size which is sufficiently small such that when the particles are formed they remain suspended in the air or gas for a sufficient amount of time such that a patient can inhale the particles or they can be delivered intranasally.

As used herein, the term "nebulizer" means a device used to reduce a liquid medication to extremely fine cloudlike particles (i.e. an aerosol). A nebulizer is useful in delivering medication to deeper parts of the respiratory tract. Nebulizers may also be referred to as atomizers and vaporizers.

The term "intranasal" or "intranasal delivery" or "intranasal administration" as used herein means delivery within or administered by way of the nasal structures.

The term "immediate-release" as used herein means that all of the pharmaceutical agent(s) is released into solution and into the biological orifice or blood or cavity etc. at the same time.

The term "targeted-release" as used herein means that the pharmaceutical agent is targeted to a specific tissue, biological orifice, tumor site or cavity, etc.

The terms "sustained-release", "extended-release", "time-release", "controlled-release", or "continuous-release" as used herein means an agent, typically a therapeutic agent or drug, that is formulated to dissolve slowly and be released over time.

As used herein the term "lyophilization" or "lyophilized" or "lyophilized powder" means a dehydration process typically used to preserve a perishable material or make the material more convenient for transport. Lyophilization works by freezing the material and then reducing the surrounding pressure to allow the frozen water in the material to sublimate directly from the solid phase to the gas phase. Other terms meaning lyophilization include freeze-drying and cryodesiccation.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model" refers to any art-accepted animal model in which the compositions of the invention exhibit efficacy.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Utility

There are no treatments for concussion injuries to the eye that restore the cellular architecture. Commotio retinae can lead to loss of central vision and permanent disability as can damage to the anterior segment of the eye. Topical application or direct injection of ACCS and/or AMP cells would be significant advances to the treatment of these concussion injuries to the eye. Intranasal administration would be an even more significant advancement by making the administration of ACCS possible by minimally trained medical personnel.

Another therapeutic utility of the subject invention is mitigation and treatment of traumatic injuries to ocular structures and the visual system and mitigation and treatment of visual dysfunction associated with traumatic brain injury, in particular, which utilizes a novel drug and a novel delivery route to treat traumatic optic neuropathy. ACCS and/or AMP cells delivered intranasally will reduce inflammation and limit or reverse axonal damage in the crushed optic nerve model, as a model of traumatic CNS nerve injury. Data suggest that treatment with ACCS and/or AMP cells could have significant potential to increase cell survival and impact axonal regeneration and thereby provide a novel treatment for eye injury following traumatic brain injury and/or traumatic optic neuropathy.

Compositions and Methods of Making Compositions

Detailed information and methods on the preparation of AMP cell compositions, generation of ACCS, generation of pooled ACCS, detection of cytokines in non-pooled and pooled ACCS using ELISA, generation of PCS compositions, and generation of sustained-release CFS compositions can be found in U.S. Pat. Nos. 8,058,066 and 8,088,732, both of which are incorporated herein by reference.

The invention provides for an article of manufacture comprising packaging material and a pharmaceutical composition of the invention contained within the packaging material, wherein the pharmaceutical composition comprises ACCS and/or AMP cells. The packaging material comprises a label or package insert which indicates that the ACCS and/or AMP cells, contained therein can be used for therapeutic applications such as, for example, treating ocular contusion and blunt injury to the eye and treating traumatic injury of the optic nerve.

Formulation, Dosage and Administration of ACCS and/or AMP Cells

Compositions comprising ACCS and/or AMP cells may be administered to a subject to provide various cellular or tissue functions, for example, to treat ocular contusion and blunt injury to the eye and treating traumatic injury of the optic nerve. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may also be administered to the recipient in one or more physiologically acceptable carriers. Carriers for ACCS and/or AMP cells may include but are not limited to solutions of normal saline, phosphate buffered saline (PBS), lactated Ringer's solution containing a mixture of salts in physiologic concentrations, or cell culture medium.

In addition, one of skill in the art may readily determine the appropriate dose of the ACCS for a particular purpose. An exemplary dose is in the range of about 0.1-to-1000 micrograms per square centimeter of applied area. Other exemplary dose ranges are 1.0-to-50.0 micrograms/applied area. In a particular embodiment, it has been found that relatively small amounts of ACCS are therapeutically useful. One exemplification of such therapeutic utility is the ability for ACCS (including pooled ACCS) to accelerate wound healing (for details see U.S. Publication No. 2006/0222634 and U.S. Pat. No. 8,187,881, both of which are incorporated herein by reference). One of skill in the art will also recognize that the number of doses to be administered needs also to be empirically determined based on, for example, severity and type of disease, disorder or injury being treated; patient age, weight, sex, health; other medications and treatments being administered to the patient; and the like. For example, in an exemplary embodiment, one dose is sufficient to have a therapeutic effect (i.e. treating ocular contusion and blunt injury to the eye and treating traumatic injury of the optic nerve). Other preferred embodiments contemplate, 2, 3, 4, or more doses for therapeutic effect.

One of skill in the art may readily determine the appropriate concentration, or dose, of the AMP cells, for a particular purpose, as well. The skilled artisan will recognize that an exemplary dose is one which produces a therapeutic effect, such as treating ocular contusion and blunt injury to the eye and treating traumatic injury of the optic nerve, in a patient in need thereof. For example, AMP cells are prepared at a concentration of between about $1 \times 10^7$-$1 \times 10^8$ cells/mL, preferably at about $2.5 \times 10^7$-$7.5 \times 10^7$ cells/mL, and most preferably at about $5 \times 10^7$ cells/mL. The volume of cell mixture administered will depend upon several variables and can only be determined by the attending physician at time of use. Such proper doses of AMP cells will require empirical determination based on such variables as the severity and type of disease, injury, disorder or condition being treated; patient age, weight, sex, health; other medications and treatments being administered to the patient; and the like. For example, in an exemplary embodiment, one dose is sufficient to have a therapeutic effect (i.e. treating ocular contusion and blunt injury to the eye and treating traumatic injury of the optic nerve). Other preferred embodiments contemplate, 2, 3, 4, or more doses for therapeutic effect.

One of skill in the art will also recognize that the number of doses (dosing regimen) to be administered needs also to be empirically determined based on, for example, severity and type of injury, disorder or condition being treated; patient age, weight, sex, health; other medications and treatments being administered to the patient; and the like. In addition, one of skill in the art recognizes that the frequency of dosing needs to be empirically determined based on similar criteria. In certain embodiments, one dose is administered every day for a given number of days (i.e. once a day for 7 days, etc.). In other embodiments, multiple doses may be administered in one day (every 4 hours, etc.). Multiple doses per day for multiple days are also contemplated by the invention.

In further embodiments of the present invention, at least one additional agent may be combined with the ACCS and/or AMP cells. Such agents may act synergistically with the ACCS and/or AMP cells of the invention to enhance the therapeutic effect. Such agents include but are not limited to growth factors, cytokines, chemokines, antibodies, inhibitors, antibiotics, immunosuppressive agents, steroids, anti-fungals, anti-virals or other cell types (i.e. stem cells or stem-like cells). Inactive agents include carriers, diluents, stabilizers, gelling agents, delivery vehicles, ECMs (natural and synthetic), scaffolds, and the like. When the ACCS and/or AMP cells are administered conjointly with other pharmaceutically active agents, even less of the ACCS and/or AMP cells may be needed to be therapeutically effective.

Aerosol Compositions

Methods for creating aerosol compositions are well known to skilled artisans. Specifics can be found in "Development of Nasal Delivery Systems: A Review" By Jack Aurora in Drug Delivery and Development, volume 2, number 7, 2002, and "Drug Delivery to the Lung" By Hans Bisgaard, Christopher O'Callaghan, Gerald C. Smaldone, published by Informa Health Care, 2001, and elsewhere in the scientific literature. Such methods are useful in creating aerosol compositions of ACCS and/or AMP cells.

ACCS and/or AMP cells may also be inserted into a delivery device, e.g., a nebulizer or atomizer or vaporizer, in different forms. For example, the ACCS and/or AMP cells can be part of a solution or a suspension contained in such a delivery device. As used herein, the term "solution" includes a pharmaceutically acceptable carrier or diluent. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and may optionally be preserved against the contaminating action of microorganisms such as bacteria and fungi through the use of, for example, parabens, chlorobutanol, phenol, ascorbic acid, thimerosal, and the like. Solutions of the invention can be prepared by incorporating the ACCS and/or AMP cells in a pharmaceutically acceptable carrier or diluent and, as required, other ingredients enumerated above. It should also be appreciated that the ACCS could also be formulated as a lyophilized dry powder or microspheres. In addition, a suspension of AMP cells could also be administered via the nasal route.

The timing of administration of ACCS and/or AMP cells will depend upon the type and severity of the disease, disorder, or injury being treated. In one embodiment, the ACCS and/or AMP cells are administered as soon as possible after diagnosis. In another embodiment, ACCS and/or AMP cells are administered more than one time following diagnosis. In certain embodiments, where surgery is required, the ACCS and/or AMP cells are administered at surgery. In still other embodiments, the ACCS and/or AMP cells are administered at as well as after surgery. Such post-surgical administration may take the form of a single administration or multiple administrations.

Support matrices, scaffolds, membranes and the like into which the ACCS and/or AMP cells can be incorporated or embedded include matrices which are recipient-compatible and that degrade into products which are not harmful to the recipient. Detailed information on suitable support matrices, etc. can be found in U.S. Pat. Nos. 8,058,066 and 8,088,732, both of which are incorporated herein by reference.

A "therapeutically effective amount" of a therapeutic agent within the meaning of the present invention will be determined by a patient's attending physician or veterinarian. Such amounts are readily ascertained by one of ordinary skill in the art and will enable treating ocular contusion and blunt injury to the eye and treating traumatic injury of the optic nerve when administered in accordance with the present invention. Factors which influence what a therapeutically effective amount will be include, the specific activity of the therapeutic agent being used, the extent of the injury, the absence or presence of infection, time elapsed since the injury, and the age, physical condition, existence of other disease states, and nutritional status of the patient. Additionally, other medication the patient may be receiving will effect the determination of the therapeutically effective amount of the therapeutic agent to administer.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

The following examples provide evidence of the anti-inflammatory and wound healing effects of ACCS and/or AMP cells is several different settings (mucosal/infected; skin (intact and lesioned); cutaneous wound/infected; and traumatic brain injury), thus providing strong evidence for the broad applicability of ACCS and/or AMP cells to a variety of conditions including treating ocular contusion and blunt injury to the eye and treating traumatic injury of the optic nerve. Because ACCS is derived from AMP cells it is expected that administration of AMP cells will be effective as well.

Example 1: Inflammatory Model—Use of ACCS to Prevent Onset of Periodontal Disease in an Animal Model Objective: The aim of this study was to evaluate the preventive role of ACCS in *Porphyromonas gingivalis* (*P. gingivalis*)-induced experimental periodontitis in rabbits Methods: Eight New-Zealand White rabbits were distributed into 3 groups: 1. Untreated (n=2), 2. Control (unconditioned ACCS culture media) (n=3), and 3. ACCS (n=3). At baseline, all rabbits received silk ligatures bilaterally tied around mandibular second premolars under general anesthesia. The assigned test materials, ACCS or control, in volumes of 10 µL were topically applied to the ligated sites with a blunt needled-Hamilton Syringe from the time of ligature; control animals received ligature, but no treatment. Topical *P. gingivalis*-containing slurry (1 mL) was subsequently applied to induce the periodontal inflammation. The application of test materials and *P. gingivalis* continued for 6 weeks on an every-other-day schedule. At 6 weeks, following euthanasia, the mandibles were surgically harvested. Morphometric, radiographic and histologic evaluations were performed.

Results: Macroscopic evaluations including soft tissue assessments, crestal bone and infrabony measurements showed significant periodontal breakdown induced by *P. gingivalis* in control and no treatment groups at 6 weeks compared to historical ligature-alone groups (p=0.05, p=0.03, respectively). ACCS application significantly inhibited soft tissue inflammation and prevented both crestal bone loss and infrabony defect formation compared to untreated and control groups (p=0.01, p=0.05, respectively). Histologic assessments and histomorphometric measurements supported the clinical findings; ACCS treated animals demonstrated significantly less inflammation in soft tissue and less bone loss compared to the untreated and control groups (p=0.05).

Conclusions: Topical ACCS application prevents periodontal inflammatory changes and bone loss induced by *P. gingivalis* as shown both at clinical and histopathological level. ACCS has potential as a therapeutic approach for the prevention of periodontal diseases Example 2: Inflammatory Model—Use of ACCS to Stop Progression of or Reverse Periodontal Disease in an Animal Model Objective: The aim of this study was to evaluate the therapeutic actions of ACCS in the treatment of periodontitis induced by *P. gingivalis*.

Methods: The study was conducted using a two-phase rabbit periodontitis protocol: 1—Disease induction (6 weeks) and 2—Treatment (6 weeks). Periodontal disease was induced in 16 New-Zealand White rabbits by every-other-day application of topical *P. gingivalis* to ligatured mandibular premolars. At the end of Phase 1, 4 randomly selected rabbits were sacrificed to serve as the baseline disease group. For Phase 2, the remaining 12 rabbits were distributed into 3 groups (n=4), 1—Untreated, 2—Control (unconditioned ACCS culture media) and 3—ACCS treatment. At the end of Phase 2, morphometric, radiographic and histologic evaluations were performed on harvested mandibles.

Results: The baseline disease group exhibited experimental periodontitis evidenced by tissue inflammation and bone loss. At the end of Phase 2, the untreated group showed significant disease progression characterized by increased soft and hard tissue destruction (p=0.05). The tissue inflammation and bone loss was significantly reduced by topical ACCS compared to baseline disease and untreated groups (p=0.05; p=0.002, respectively). The control treatment also arrested disease progression compared to untreated group (p=0.01), but there was no improvement in periodontal health compared to baseline disease (p=0.4). Histopathological assessments revealed similar findings; ACCS stopped the progression of inflammatory process (p=0.003) and reversed bone destruction induced by *P. gingivalis* (p=0.008). The ACCS-treated group had minimal osteoclastic activity limited to crestal area compared to untreated and control groups, which showed a profound osteoclastogenic activity at the bone crest as well as at interproximal sites.

Conclusions: Topical application of ACCS stopped the progression of periodontal inflammation and resulted in tissue regeneration in rabbit periodontitis indicating its potential therapeutic efficacy.

Example 3: Evaluate the Efficacy of Topically Applied ACCS to Inhibit Irritant 12-O-tetradecanoylphorbol-13-acetate (TPA) Skin Inflammation in Mice Method: Topical treatment was given twice daily to the following groups: 1. TPA+topical control; 2. TPA+ACCS; 3. TPA+clobetasol 0.05 topical solution (the strongest available topical corticosteroid); 4. ACCS alone; 5. No treatment (the other untreated ear was measured). The endpoints for the study were ear thickness and ear weight at the end of the experiment. The thicker the ear and the more it weighs correlates with the degree of inflammation.

Results: Topically applied ACCS was effective at reducing the inflammation induced by TPA. The anti-inflammatory activity of topical ACCS reached the same level as clobetasol (a class 1 potent topical corticosteroid) by 3 days after beginning application.

Conclusion: ACCS has a strong anti-inflammatory effect when applied to skin.

Example 4: Evaluate the Efficacy of Intralesional Injection of ACCS to Inhibit Irritant (TPA) Skin Inflammation in Mice Method: Intralesional injection into the ear was given once daily to the following groups: 1. TPA+intralesional control; 2. TPA+intralesional ACCS; 3. TPA+intralesional kenalog (10 mg/ml) (a potent intralesional corticosteroid); 4. ACCS intralesional injection alone; 5. Saline sham injections to the normal untreated ear. The endpoints for the study were ear thickness and ear weight at the end of the experiment. The thicker the ear and the more it weighs correlates with the degree of inflammation.

Results: Intralesional injection of ACCS was effective at reducing the inflammation induced by TPA at all timepoints beginning on day 2 of daily injections. Intralesional kenalog (10 mg/ml) injections induced a hematoma at the site of injection, which led to some inflammation and that is why there is not a substantial difference in ear thickness when comparing TPA+kenalog with TPA+control.

Conclusions: Intralesional ACCS did reduce skin inflammation but the topically applied ACCS in Example 1 above had a more potent effect. There was no difference in ear weight using either ACCS or intralesional kenalog compared with TPA+control.

Example 5: Effects of ACCS in an Animal Model of Chronic Wound Healing

Model: An art-accepted animal model for chronic granulating wound was used to study the effects of ACCS on chronic wound healing (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990.).

Results: ACCS was effective in not allowing proliferation of tissue bacterial bioburden. ACCS allowed accelerated healing of the granulating wound significantly faster than the non-treated infected control groups (Franz, M., et al., ePlasty Vol. 8, pp. 188-199, Apr. 11, 2008).

Example 6: Intranasal Delivery of $^{125}$I-Labeled ACCS

Model: $^{125}$I-labeled ACCS was administered intranasally to rats.

Results: Significant quantities of $^{125}$I-labeled ACCS delivered intranasally were deposited on the rat optic nerve (1000 ng ACCS/g tissue) and vitreous (900 ng ACCS/g tissue) as compared to blood (100 ng ACCS/g tissue), olfactory bulb (50 ng ACCS/g tissue) and trigeminal nerve (25 ng ACCS/g tissue). Thus, intranasally delivered ACCS represents a novel and feasible approach to treat numerous visual deficiencies as a result of traumatic brain injury in the military as well as in the civilian population.

Example 7: Treatment with AMP Cells as a Neuroprotective Therapy for Traumatic Brain Injury Method: AMP cells were tested in a rat model of Penetrating Ballistic-like Brain Injury (PBBI) (Williams, A. J., 2005, "Characterization of a New Rat Model of Penetrating Ballistic Brain Injury", J Neurotrauma 22; 3:313-331) to test their neuroprotective potential. The AMP cells were labeled with fluorescent dye PKH26 (as described above) after two passages, suspended in conditioned medium, and injected in rats ($2\times10^6$ cells/50 µl/rat) immediately following right frontal PBBI or sham PBBI surgery by ipsilateral i.c.v. administration ($2\times10^6$ cells/50 µl/rat). PBBI controls received i.c.v. injection of PBS, control medium, or conditioned medium (50 µl/rat). After 3 weeks' survival, severe necrotic injury developed along the PBBI track and no significant difference in injury volume has been observed in all treatment groups.

Results: In non-AMP cell treated PBBI rats, silver stained axonal degeneration was prominent along the corpus callosum and in the ipsilateral thalamus. In contrast, the AMP cell treatment significantly attenuated axonal degeneration in both of these areas. Interestingly, PKH26 labeled AMP cells were detected only in the subventricular zone (SVZ) and the corpus callosum (parallel with the axonal degeneration), but not in the thalamus, and none of these labeled AMP cells appeared to express neural differentiation evidenced by the lack of double labeling with GFAP and MAP-2 immunostaining No migration and neuronal differentiation of AMP cells was detected in the non-injury control group although cells did survive at the injection site. These results indicate that AMP cell migration is specifically induced by PBBI and requires SVZ homing, yet the neuroprotective effect of i.c.v. treatment of AMP cells is not limited to the area where migrated AMP cells are present, suggesting that the attenuation of the secondary brain injury following PBBI is likely to be mediated by mechanisms other than cell replacement, possibly through sustained secretion of neurotrophic factors which AMP cells are known to secrete in physiological levels and in a physiologically relevant temporal fashion.

Example 8: Treatment with AMP Cells in Combination with Collagen-Based Matrix as a Neuroprotective Therapy for Traumatic Brain Injury Model: One of the histopathological consequences of a penetrating ballistic-like brain injury (PBBI) is the permanent brain cavitation that becomes unsalvageable once it develops. In Example 7 above, AMP cells suspended in conditioned media injected directly in the injury tract/brain cavity failed to survive. This was likely due to the absence of a supportive matrix at the localized wound site. Thus, AMP cells were seeded in a collagen-based scaffold prior to injection to investigate AMP cell survival and the neuroprotective support they may provide in the rat PBBI model.

Method: AMP cells, labeled with the fluorescent dye PKH26, were either suspended in conditioned medium or a liquefied collagen matrix ($2\times10^6$ cells/150 µL/rat) that solidifies at 37° C. Control rats received only the liquefied collagen matrix (150 µL/rat). Injections were delivered along the PBBI tract (from the frontal cortex through the dorsal striatum) immediately after injury (n=5/grp). Serial sections of the injury site and surrounding areas of the brain were prepared two weeks post-injury.

Results: Consistent with previous results, AMP cells suspended in the conditioned medium failed to survive at the injury site. In contrast, AMP cells seeded in the collagen-based scaffold survived and were present in the injury cavity. Labeled AMP cells were also found in the subventricular zone of the lateral ventricle and in the corpus callosum. Importantly, the AMP cell/collagen treatment significantly attenuated PBBI-induced axonal degeneration (as determined by silver staining) in the corpus callosum and ipsilateral thalamus, compared to controls.

Conclusion: A solidified collagen-based scaffold provided a supportive matrix for AMP cell survival, migration, and neuroprotection when injected along the PBBI tract immediately after injury.

Example 9: Evaluation of ACCS to Treat Ocular Contusion and Blunt Injury to the Eye Model: Blunt injuries to animal porcine eyes are caused by either paint balls or air gun pellets causing concussion injury to the intraocular contents. ACCS is administered by three routes: intranasal (see, for example, Wong, Y. and Zuo, Z., Brain disposition and catalepsy after intranasal delivery of loxapine: role of metabolism in PK/PD of intranasal CNS drugs, Pharm Res 30(9):2368-2384, (2013); Thorne R G, Hanson L R, Ross T M, Tung D, Frey W H $2^{nd}$, Delivery of interferon-beta to the monkey nervous system following intranasal administration Neuroscience, March 27; 152(3): 785-97, doi: 10.1016/j.neuroscience.2008.01.013. Epub 2008, Jan. 16, 2008; and Renner D B, Svitak A L, Gallus N J, Ericson M E, Frey W H 2nd, Hanson L R, Intranasal delivery of insulin via the olfactory nerve pathway, J Pharm Pharmacol doi: 10.1111/j.2042-7158.2012.01555.x., 1709-1714, 2012), topical drops, and intraocular injection. As set forth in Example 6 above, radioactively-labelled ACCS is found primarily in the optic nerve and vitreous humor after intranasal delivery. Ocular coherence tomography (OCT) and direct visualization with photographs is used to evaluate the damage in eyes after trauma and to track any reparative process over a 3-month period after injury. Histology of the eyes is evaluated at 3 months. The OCT evaluation is the primary endpoint for the retina, as has been reported in humans (see, for example, Seong Joon Ahn, Optical Coherence Tomography Morphologic Grading of Macular Commotio Retinae and its Association With Anatomic and Visual Outcomes, American Journal of Ophthalmology 156, Issue 5, 994-1001, 2013). Other than human studies, previous animal studies have often dealt with enucleated eyes, as there have been no known treatments for these injuries. This study is novel and does not duplicate any previous animal or human study.

Example 10: Traumatic Optic Neuropathy Animal Model

Model: Traumatic optic neuropathy is modeled in rodents by crushing the nerve with forceps, resulting in loss of vision and degeneration of retinal ganglion cells (RGCs) (see, for example, Zuo, et al., "SIRT1 promotes RGC survival and delays loss of function following optic nerve crush", Invest Ophthalmol Vis Sci 54(7):5097-5102, 2013)). RGC function is measured by pupillometry and optokinetic responses, and RGC survival is quantified, showing that this model provides a unique opportunity to assess neuroprotective therapies for traumatic CNS injuries.

Method: ACCS is administered intranasally to mice (Hanson, et al., "Intranasal administration of CNS therapeutics to awake mice", J Vis Exp 74(e4440):1-7, 2013) daily for 1, 2, or 4 weeks post-optic nerve crush. Optic nerve inflammation, demyelination and axonal injury are assessed by histologic and immunohistochemical staining of optic nerve sections as in prior studies (Shindler, et al., "Inflammatory demyelination induces axonal injury and retinal ganglion cell apoptosis in experimental optic neuritis", Exp Eye Res 87(3):208-213, 2008). Terminal deoxynucleotidyl transferase-mediated biotinylated UTP nick end labeling (TUNEL), a marker of apoptosis, is used to identify dying RGCs. ACCS is packaged in a specialized nasal delivery device such as Kurve Technology's ViaNase.

Example 11: Neuroprotective Effects of Amnion-Derived Cellular Cytokine Solution (ACCS) in Experimental Optic Neuritis Optic neuritis is a demyelinating inflammation of the optic nerve that often occurs in multiple sclerosis (MS) patients. Loss of retinal ganglion cells (RGCs) and their axons also occurs in optic neuritis, and correlates with permanent vision loss. ACCS is a novel biologic mixture of growth factors and cytokines secreted from Amnion-derived Multipotent Progenitor (AMP) cells, that exhibits anti-inflammatory and neuroprotective properties in a variety of disease models. The ability of ACCS to suppress optic neuritis in the experimental autoimmune encephalomyelitis (EAE) model of MS was examined.

Method: EAE was induced in C57/BL6 mice by immunization with myelin oligodendroglial glycoprotein peptide. Mice were treated daily with one drop (6 uL) of ACCS intranasally beginning before or after onset of optic neuritis. Visual function was assessed by optokinetic responses (OKR) at baseline, then weekly until sacrifice 6 weeks post-immunization. Retinas and optic nerves were isolated. RGCs were immunolabeled with Brn3a antibodies to quantify RGC survival. Inflammation was assessed by H&E and Iba1 (macrophage/microglia marker) staining, demyelination by luxol fast blue staining, and axonal loss by neurofilament staining of optic nerve sections.

Results: Progressive decreases in OKR occurred in vehicle-treated EAE mice, along with significant RGC loss, consistent with prior studies showing onset of optic neuritis occurring 12-15 days after EAE induction. Daily intranasal ACCS treatment beginning on day 0 (day of immunization), 15, 22, or 30, significantly reduced the level of vision loss, and treatment from day 0 or day 15 significantly attenuated RGC loss. ACCS also decreased the degree of demyelination and axonal loss, but had limited effects on the level of inflammation in the optic nerve.

Conclusions: ACCS treatment attenuates RGC loss, preserves OKR responses, and reduces demyelination and axonal loss during experimental optic neuritis in EAE mice. ACCS exerts effects with treatment initiated before and after onset of optic neuritis, suggesting it may be useful as a preventative or abortive therapy. Results suggest ACCS is a potential treatment for optic neuritis that warrants further study. Furthermore, potent effects seen after intranasal administration suggest this may be a novel drug delivery method for optic neuritis.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for treating concussive injuries to the eye in a patient in need thereof comprising administering to the patient a therapeutically effective amount of a composition selected from the group consisting of Amnion-derived Cellular Cytokine Solution (ACCS) and Amnion-derived Multipotent Progenitor (AMP) cells.

2. The method of claim 1 wherein the ACCS or the AMP cells are formulated for intranasal administration, topical administration or administration by intraocular injection.

3. The method of claim 2 wherein the intranasal administration is aerosol or spray administration.

4. The method of claim 1 wherein the ACCS is formulated as a lyophilized dry powder nasal formulation.

5. The method of claim 1 wherein the concussive injury to the eye is selected from the group consisting of ocular contusion and blunt injury to the eye.

6. A method for treating traumatic injury of the optic nerve in a patient in need thereof comprising administering to the patient a therapeutically effective amount of a composition selected from the group consisting ACCS and AMP cells.

7. The method of claim 6 wherein the ACCS or the AMP cells are formulated for intranasal administration.

8. The method of claim 7 wherein the intranasal administration is aerosol or spray administration.

9. The method of claim 6 wherein the ACCS is formulated as a lyophilized dry powder nasal formulation.

10. A method for ameliorating optic nerve degeneration following concussive injury to the eye in a patient in need thereof comprising administering to the patient a therapeutically effective amount of a composition selected from the group consisting of ACCS and AMP cells.

11. The method of claim 10 wherein the ACCS or the AMP cells are formulated for intranasal administration.

12. The method of claim 11 wherein the intranasal administration is aerosol or spray administration.

13. The method of claim 10 wherein the ACCS is formulated as a lyophilized dry powder nasal formulation.

14. The method of claim 10 wherein the concussive injury to the eye is selected from the group consisting of ocular contusion and blunt injury to the eye.

* * * * *